US012766157B2

(12) United States Patent
Blanchard et al.

(10) Patent No.: US 12,766,157 B2
(45) Date of Patent: Oct. 20, 2026

(54) NUTRITIONAL COMPOSITION

(71) Applicant: SOCIETE DES PRODUITS NESTLE S.A., Vevey (CH)

(72) Inventors: Carine Blanchard, Le Mont-sur-Lausanne (CH); Cheong Kwet Choy Kwong Chung, Lausanne (CH); Sebastien Holvoet, Montpreveyres (CH); Dominique Sandra Donnicola, Servion (CH)

(73) Assignee: Societe des Produits Nestle S.A., Vevey (CH)

( * ) Notice: Subject to any disclaimer, the term of this patent is extended or adjusted under 35 U.S.C. 154(b) by 613 days.

(21) Appl. No.: 18/252,077

(22) PCT Filed: Nov. 9, 2021

(86) PCT No.: PCT/EP2021/081150

§ 371 (c)(1),
(2) Date: May 8, 2023

(87) PCT Pub. No.: WO2022/101222

PCT Pub. Date: May 19, 2022

(65) Prior Publication Data

US 2024/0009216 A1 Jan. 11, 2024

(30) Foreign Application Priority Data

Nov. 10, 2020 (EP) .................................... 20206583

(51) Int. Cl.

| | |
|---|---|
| ***A61K 31/702*** | (2006.01) |
| ***A23C 9/20*** | (2006.01) |
| ***A23L 33/00*** | (2016.01) |
| ***A23L 33/125*** | (2016.01) |
| ***A61P 37/06*** | (2006.01) |

(52) U.S. Cl.

CPC ............ *A61K 31/702* (2013.01); *A23C 9/203* (2013.01); *A23L 33/125* (2016.08); *A23L 33/40* (2016.08); *A61P 37/06* (2018.01)

(58) Field of Classification Search

None

See application file for complete search history.

(56) References Cited

U.S. PATENT DOCUMENTS

| | | | | |
|---|---|---|---|---|
| 2012/0171166 | A1 * | 7/2012 | Chow | A23L 33/40 424/93.4 |
| 2016/0243139 | A1 * | 8/2016 | Vigsnæs | A61K 31/7004 |
| 2018/0368460 | A1 | 12/2018 | Mcconnell et al. | |
| 2019/0054165 | A1 * | 2/2019 | Blanchard | A23L 33/40 |
| 2020/0206250 | A1 | 7/2020 | Mcconnell et al. | |
| 2020/0206251 | A1 | 7/2020 | Buck et al. | |

FOREIGN PATENT DOCUMENTS

| | | |
|---|---|---|
| CN | 108289492 A | 7/2018 |
| WO | 2017129640 | 8/2017 |
| WO | 2019087140 | 5/2019 |
| WO | 2019232513 | 12/2019 |

OTHER PUBLICATIONS

Takatsu "Interleukin-5 and IL-5 receptor in health and diseases" Proc. Jpn. Acad., Ser. B, 2011, vol. 87, pp. 463-485.

Roufosse "Targeting the Interleukin-5 Pathway for Treatment of Eosinophilic Conditions Other than Asthma" Frontiers in Medicine, Apr. 2018, vol. 5, article 49, 27 pages.

Chinese Office Action for Appl No. 202180069568.7 dated Mar. 21, 2026, 6 pages.

Gdalevich et al., "Breast-Feeding and the Onset of Atopic Dermatitis in Childhood: A Systematic Review and Meta-Analysis of Prospective Studies", Journal of the American Academy of Dermatology, vol. 45, Issue No. 4, Oct. 2001, pp. 520-527.

European Office Action for Appl No. 21 805 966.5-1105 dated Jul. 3, 2026, 7 pages.

* cited by examiner

*Primary Examiner* — Dale R Miller

(74) *Attorney, Agent, or Firm* — K&L Gates LLP

(57) ABSTRACT

A nutritional composition comprising the human milk oligosaccharides (HMOs) 2'-fucosyllactose (2FL), 3'-fucosyllactose (3FL), 3'-sialyllactose (3SL), and lacto-N-neotetraose (LNnT). The nutritional composition is useful for treating or preventing disorders associated with an above-normal number of granulocytes in a tissue. For example, the combinations may have utility in preventing or treating eosinophilic gastrointestinal diseases.

11 Claims, 3 Drawing Sheets

NUTRITIONAL COMPOSITION

CROSS REFERENCE TO RELATED APPLICATIONS

The present application is a National Stage of International Application No. PCT/EP2021/081150, filed on Nov. 9, 2021, which claims priority to European Patent Application No. 20206583.5, filed on Nov. 10, 2020, the entire contents of which are being incorporated herein by reference.

FIELD OF THE INVENTION

The present invention relates to nutritional compositions for use in treating or preventing disorders associated with an above-normal number of granulocytes in a tissue and/or degranulation of granulocytes. In particular, the invention relates to nutritional compositions comprising the human milk oligosaccharides (HMOs) 2'-fucosyllactose (2FL), 3'-fucosyllactose (3FL), 3'-sialyllactose (3SL), lacto-N-neotetraose (LNnT), and optionally 6'-sialyllactose (6SL) and lacto-N-tetraose (LNT).

BACKGROUND TO THE INVENTION

An increased number of granulocytes, and/or increased activation of granuloctyes such as eosinophils, basophils or mast cells, in a tissue is associated with a number of disorders, like various gastrointestinal disorders, food allergies, and atopic dermatitis.

For example, eosinophilic esophagitis (EoE) is a chronic, immune-mediated, inflammatory condition of the esophagus. EoE is today considered to be the most common cause of chronic esophagitis after gastroesophageal reflux disease (GERD), and the leading cause of dysphagia in children and young adults. Symptoms of EoE include functional abdominal pain, vomiting, difficultly to thrive, swallowing difficulty, food impaction, and heartburn. The disease was initially described in children but occurs in adults as well. Eosinophils are usually not found in normal esophageal mucosa. However, in eosinophilic esophagitis the eosinophils infiltrate the epithelium of the esophagus and can often be found in clusters close to the surface of the epithelium. Frequently the infiltration of the eosinophils is associated with a thickening of the basal layer as a reaction to the inflammatory activities in the epithelium. Mast cells and basophils are granulocytes that are also increased in eosinophilic gastrointestinal disorders and are part of the pathogenesis.

Allergic inflammation is a fundamental pathological change of an allergy. There are two phases in the basic process of allergic inflammation: the induction (sensitization) phase and the effector phase. The induction phase involves antigen presenting cells (APCs), T cells, TH2 cytokines, such as interleukin (IL)-4, IL-5 and IL-13, class switching of B cells, IgE secretion and binding to the high-affinity IgE receptor FcεRI on the membrane of mast cells and basophils, forming sensitized mast cells and basophils. Notably, IL-5 is a cytokine responsible for the differentiation and survival of eosinophils and animals lacking IL5 are largely depleted in tissue eosinophils. When the sensitized individual is re-exposed to the same allergen that initiated the response, the IgE is able to bind to that allergen. The effector phase occurs when the same allergen cross-links two adjacent IgEs on sensitized mast cells or basophils. The activated mast cells or basophils subsequently undergo degranulation, releasing proinflammatory mediators or cytokines, thereby causing the clinical manifestations of allergy. Soluble allergens, IgEs and mast cells or basophils are key factors in the pathophysiological process of allergic inflammation, representing causative factors, messengers and primary effector cells, respectively. In contrast to basophils and mast cells, eosinophils and neutrophils are secondary effector cells, which can accumulate and be activated through the mediators released from mast cells or basophils. In a similar mechanism, degranulation of activated eosinophils releases preformed mediators such as major basic protein, and enzymes such as peroxidase.

There are different strategies available for the treatment of disorders associated with an above-normal number of granulocytes in a tissue including medical therapy, mechanical dilatation, and modification of the diet.

In medical therapy of EoE corticosteroids and proton pump inhibitors have been found to mitigate the symptoms granulocyte infiltration. It has also been observed that the allergic response can be reduced by the administration of antihistamines. Mechanical dilatation of the esophagus might be considered in severe cases where the swelling of the epithelium is threatening to block the esophagus. Such therapies are generally not used infants or children.

Previous nutritional treatment regimens mainly aim at elimination of the allergen (or causative foods) from the diet. Dietary modification often leads to use of hypoallergenic protein compositions like compositions only comprising free amino acids or extensively hydrolyzed protein. For example, US 2008/0031814 describes a nutritional composition lacking allergenic ingredients and thereby preventing the development of allergic inflammatory conditions. Thus, instead of treating the disease by the choice of certain nutritional ingredients the diets of the prior art aim at avoiding allergenic ingredients in the diet.

Therefore, there is a need for a nutritional composition comprising natural compounds that does not only lack main allergens but can actively prevent or treat food induced gastrointestinal inflammatory diseases such as eosinophilic gastro-intestinal disorders (EGID) and/or other IgE or non-IgE associated allergic eosinophilic disorders particularly for allergic infants and/or children suffering from such disorders. EGID include Eosinophilic esophagitis, eosinophilic gastritis, eosinophilic enthero-colitis and eosinophilic colitis.

SUMMARY OF THE INVENTION

The present inventors have surprisingly found that specific combinations of HMOs are most efficacious in inhibiting IL-5 and/or stabilizing granulocytes. The combinations have utility in treating or preventing disorders associated with an above-normal number of granulocytes in a tissue and/or degranulation of granulocytes. For example, the combinations may have utility in preventing or treating eosinophilic gastrointestinal diseases and other IgE and non-IgE associated allergic eosinophil disorders.

Accordingly, in one aspect, the invention provides a nutritional composition comprising the human milk oligosaccharides (HMOs) 2'-fucosyllactose (2FL), 3'-fucosyllactose (3FL), 3'-sialyllactose (3SL), and lacto-N-neotetraose (LNnT).

In some embodiments, the HMOs in the nutritional composition consist of, or consist essentially of, 2FL, 3FL, 3SL, and LNnT.

In some embodiments, the HMOs in the nutritional composition consist of, or consist essentially of:

i. about 40 wt % to about 80 wt % of 2FL, preferably about 55 wt % to about 75 wt %, preferably about 65 wt % to about 70 wt %;
ii. about 2 wt % to about 15 wt % of LNnT, preferably about 4 wt % to about 12 wt %, preferably about 6 wt % to about 9 wt %;
iii. about 5 wt % to about 30 wt % 3FL, preferably about 10 wt % to about 25 wt %, preferably about 15 wt % to about 20 wt %; and
iv. about 2 wt % to about 15 wt % of 3SL; preferably about 4 wt % to about 12 wt %, preferably about 7 wt % to about 9 wt %.

In some embodiments, the total amount of 2FL, 3FL, 3SL, and LNnT present in the nutritional composition is at a concentration of between 10 μg/ml and 10000 μg/ml, preferably between 50 μg/ml and 5000 μg/ml.

In another aspect, the invention provides a nutritional composition comprising the human milk oligosaccharides (HMOs) 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT).

In some embodiments, the HMOs in the nutritional composition consist of, or consist essentially of, 2FL, 3FL, 3SL, LNnT, 6SL and LNT.

In some embodiments, the HMOs in the nutritional composition consist of, or consist essential of:

i. about 35 wt % to about 60 wt % of 2FL, preferably about 40 wt % to about 50 wt %, preferably about 43 wt % to about 47 wt %;
ii. about 1 wt % to about 10 wt % of LNnT, preferably about 3 wt % to about 7 wt %, preferably about 4 wt % to about 6 wt %;
iii. about 10 wt % to about 30 wt % of LNT, preferably about 15 wt % to about 25 wt %, preferably about 18 wt % to about 22 wt %;
iv. about 3 wt % to about 20 wt % 3FL, preferably about 7 wt % to about 15 wt %, preferably about 10 wt % to about 13 wt %;
v. about 1 wt % to about 10 wt % of 3SL, preferably about 4 wt % to about 8 wt %, preferably about 5 wt % to about 7 wt %; and
vi. about 5 wt % to about 20 wt % of 6SL, preferably about 7 wt % to about 15 wt %, preferably about 10 wt % to about 14 wt %.

In some embodiments, the total amount of 2FL, 3FL, 3SL, LNnT, 6SL and LNT present in the nutritional composition is at a concentration of between 10 μg/ml and 10000 μg/ml, preferably between 50 μg/ml and 5000 μg/ml.

In an embodiment, the nutritional composition of the invention is preferably for administration to an infant or a young child.

In an embodiment, the nutritional composition may be in the form of an infant formula, a starter infant formula, a follow-on or follow-up infant formula, a growing-up milk, a fortifier or a supplement. In one embodiment, the nutritional composition of the invention is an infant formula or a young-child formula.

In some embodiments, the nutritional composition of the invention is an extensively hydrolysed formula (eHF) or an amino acid-based formula (AAF).

In some embodiments, the nutritional composition of the invention comprises:

(a) 1.8-3.2 g protein per 100 kcal;
(b) 9-14 g carbohydrate per 100 kcal; and/or
(c) 4.0-6.0 g fat per 100 kcal.

In some embodiments, the nutritional composition of the invention comprises about 2.4 g or less protein per 100 kcal.

In some embodiments, the nutritional composition of the invention comprises 1.8-2.4 g protein per 100 kcal, 2.1-2.3 g protein per 100 kcal, or 2.15-2.25 g protein per 100 kcal.

In some embodiments, the nutritional composition comprises about 2.2 g protein per 100 kcal.

In some embodiments, about 30% or less by weight of the fat in the nutritional composition of the invention is medium-chain triglycerides (MCTs).

In some embodiments, the nutritional composition is a supplement. In one embodiment, the total amount of 2FL, 3FL, 3SL, and LNnT present in the supplement may be in an amount of 0.2 g to 2 g per unit dose of the supplement, preferably about 0.4 g to 1.5 g per unit dose, preferably between 0.5 g and 1 g per unit dose. In one embodiment, the total amount of 2FL, 3FL, 3SL, LNnT, 6SL and LNT present in the supplement may be in an amount of 0.2 g to 2 g per unit dose of the supplement, preferably about 0.4 g to 1.5 g per unit dose, preferably between 0.5 g and 1 g per unit dose.

In another aspect, there is provided a nutritional composition as defined herein for use in treating or preventing a disorder associated with an above-normal number of granulocytes in a tissue and/or degranulation of granulocytes.

In one aspect, the invention provides a method of treating or preventing a disorder associated with an above-normal number of granulocytes in a tissue and/or degranulation of granulocytes in a subject, comprising administering to the subject a nutritional composition as defined herein.

In one aspect, there is provided a nutritional composition as defined herein for use in preventing or treating eosinophilic gastrointestinal disorders, allergies, in particular, food allergies, a gastrointestinal syndrome, allergy associated with aeroallergen including asthma and allergic rhinitis, lung allergic inflammation or skin atopic dermatitis.

In one aspect there is provided a method of preventing or treating eosinophilic gastrointestinal disorders, allergies, in particular, food allergies, a gastrointestinal syndrome, allergy associated with aeroallergen including asthma and allergic rhinitis, lung allergic inflammation or skin atopic dermatitis in a subject, the method comprising administering to the subject a nutritional composition as defined herein.

In an embodiment, the eosinophilic gastrointestinal disorder is selected from the group consisting of eosinophilic esophagitis, eosinophilic gastritis, eosinophilic gastroenteritis, or eosinophilic colitis.

In a specific embodiment, the eosinophilic gastrointestinal disorder is eosinophilic esophagitis.

In another aspect, the invention provides a method of decreasing the expression of interleukin IL-5 in a subject comprising administering a nutritional composition as defined herein to the subject.

Preferably the subject is an infant or child.

DETAILED DESCRIPTION OF THE INVENTION

Figure 1:
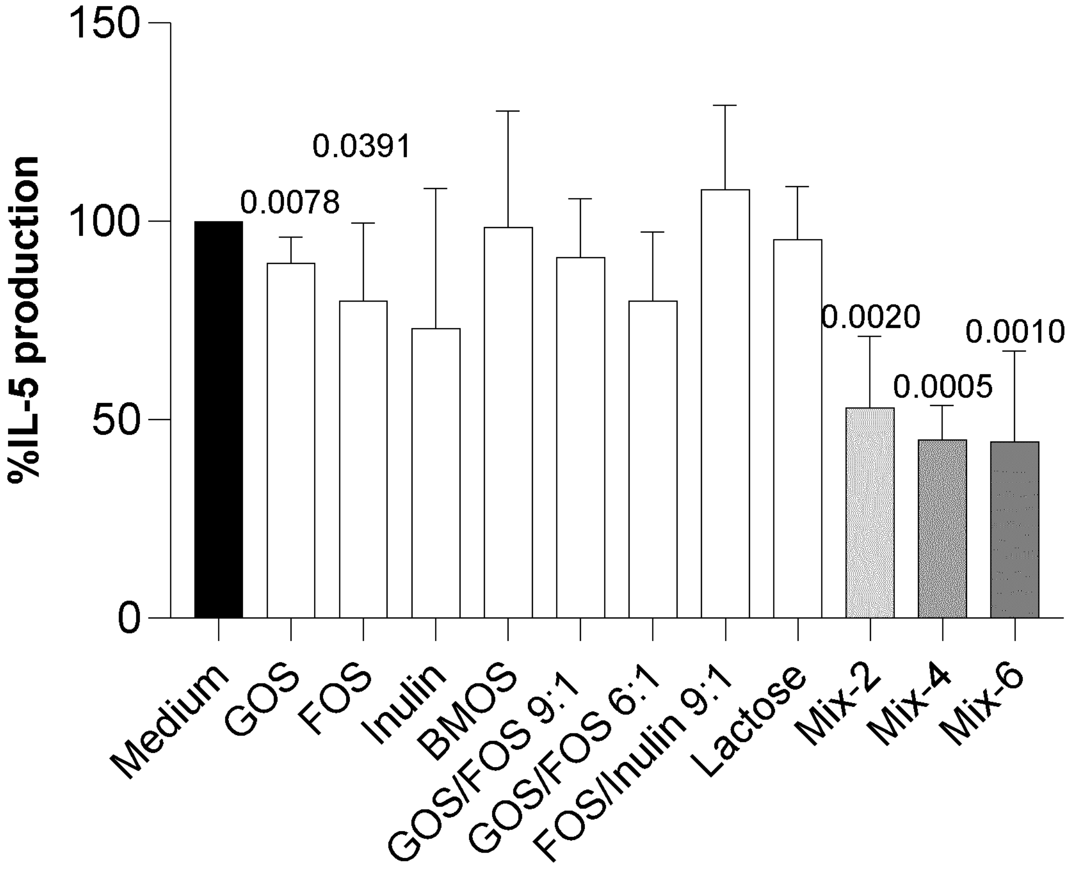
FIG. 1—HMOs decrease IL-5 expression levels in peripheral blood mononuclear cells (PBMCs). PBMCs were skewed toward a TH2 phenotype and different HMO mixes were tested. The level of IL-5 was quantified in the supernatants following incubation with different HMO mixes or regular prebiotic fibers.

It must be noted that as used herein and in the appended claims, the singular forms "a", "an", and "the" include plural referents unless the context clearly dictates otherwise.

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the terms "consisting of" and "consisting essentially of".

The term "consisting essentially of" as used herein means that any additional, non-recited members, elements or steps do not materially affect the characteristics of the claimed apparatus, composition, method, etc. Suitably, a composition comprising HMOs which "consist essentially of" recited HMOs may comprise trace amounts of non-recited HMOs (e.g. less than 1% by weight, less by 0.5% by weight, or less than 0.1% by weight of total HMOs) which do not materially affect the characteristics of the composition.

As used herein the term "about" means approximately, in the region of, roughly, or around. When the term "about" is used in conjunction with a numerical value or range, it modifies that value or range by extending the boundaries above and below the numerical value(s) set forth. In general, the terms "about" and "approximately" are used herein to modify a numerical value(s) above and below the stated value(s) by 10%.

The publications discussed herein are provided solely for their disclosure prior to the filing date of the present application. Nothing herein is to be construed as an admission that such publications constitute prior art to the claims appended hereto.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Nutritional Composition

The expression "nutritional composition" means a composition which nourishes a subject.

This nutritional composition is usually to be taken orally and it usually includes a lipid or fat source and a protein source.

In a particular embodiment, the nutritional composition is a synthetic nutritional composition. The expression "synthetic nutritional composition" means a mixture obtained by chemical and/or biological means, which can be chemically identical to the mixture naturally occurring in mammalian milks (i.e. the synthetic nutritional composition is not breast milk).

In a preferred embodiment, the nutritional composition is for an infant or young child. The infant may be, for example, 0-1 years of age or 0-6 months of age. The child may be, for example, 1-3 years of age. In a particularly preferred embodiment, the nutritional composition is an infant formula or a young-child formula.

The term "infant formula" may refer to a foodstuff intended for particular nutritional use by infants during the first year of life and satisfying by itself the nutritional requirements of this category of person, as defined in European Commission Regulation (EU) 2016/127 of 25 Sep. 2015.

The expression "infant formula" encompasses both "starter infant formula" and "follow-up formula" or "follow-on formula".

A "follow-up formula" or "follow-on formula" is given from the $6^{th}$ month onwards.

The infant formula of the present invention may be a hypoallergenic infant formula. The infant formula of the present invention may be an extensively hydrolysed infant formula (eHF) or an amino acid-based infant formula (AAF). Alternatively, the infant formula may be a partially hydrolysed infant formula (pHF).

The term "extensively hydrolysed formula" or "eHF" may refer to a formula comprising extensively hydrolysed protein. The eHF may be a hypoallergenic infant formula which provides complete nutrition for infants who cannot digest intact cow's milk protein (CMP) or who are intolerant or allergic to CMP.

The term "amino acid-based formula" or "AAF" may refer to a formula comprising only free amino acids as a protein source. The AAF may contain no detectable peptides. The AAF may be a hypoallergenic infant formula which provides complete nutrition for infants with food protein allergy and/or food protein intolerance. For example, the AAF may be a hypoallergenic infant formula which provides complete nutrition for infants who cannot digest intact CMP or who are intolerant or allergic to CMP, and who may have extremely severe or life-threatening symptoms and/or sensitisation against multiple foods.

A "hypoallergenic" composition is a composition which is unlikely to cause allergic reactions. A hypoallergenic infant formula may be tolerated by more than 90% of infants with CMP allergy. This is in line with the guidance provided by the American Academy of Pediatrics (Committee on Nutrition, 2000. Pediatrics, 106(2), pp. 346-349). Such an infant formula may not contain peptides which are recognized by CMP-specific IgE e.g. IgE from subjects with CMPA.

Infants can be fed solely with the infant formula or the infant formula can be used as a complement of human milk.

The term "young-child formula" may refer to a foodstuff intended to partially satisfy the nutritional requirements of young children ages 1 to 3 years. The expression "young-child formula" encompasses "toddler's milk", "growing up milk", or "formula for young children". The ESPGHAN Committee on Nutrition has recently reviewed the young-child formula (Hojsak, I., et al., 2018. Journal of pediatric gastroenterology and nutrition, 66(1), pp. 177-185). Suitably, a young-child formula may meet the compositional requirements proposed in Hojsak, I., et al., 2018. Journal of pediatric gastroenterology and nutrition, 66(1), pp. 177-185 and/or Suthutvoravut, U., et al., 2015. Annals of Nutrition and Metabolism, 67(2), pp. 119-132.

The young-child formula of the present invention may be a hypoallergenic young-child formula. The young-child formula of the present invention may be an extensively hydrolysed young-child formula or an amino acid-based young-child formula. Alternatively, the young-child formula may be a partially hydrolysed young-child formula (pHF).

The infant formula or a young-child formula of the invention may be in the form of a powder or liquid.

The liquid may be, for example, a concentrated liquid formula or a ready-to-feed formula. The formula may be in the form of a reconstituted infant or young-child formula (i.e. a liquid formula that has been reconstituted from a powdered form). The concentrated liquid infant or young-child formula is preferably capable of being diluted into a liquid composition suitable for feeding an infant or child, for example by the addition of water.

In some embodiments, the infant or young-child formula is in a powdered form. The powder is capable of being reconstituted into a liquid composition suitable for feeding an infant or child, for example by the addition of water.

The nutritional composition may have an energy density of about 60-72 kcal per 100 mL, when formulated as instructed. Suitably, the nutritional composition may have an energy density of about 60-70 kcal per 100 mL, when formulated as instructed.

The nutritional composition according to the invention can be for example an infant formula, a starter infant formula, a follow-on or follow-up formula, a fortifier such as a human milk fortifier, or a supplement. In some particular embodiments, the composition of the invention is an infant formula, a young-child formula or a supplement. In one preferred embodiment the nutritional composition of the invention is an infant formula.

Within the context of the present invention, the term "fortifier" refers to a composition which comprises one or more nutrients having a nutritional benefit for infants. By the term "milk fortifier", it is meant any composition used to fortify or supplement either human breast milk, infant formula, growing-up milk or human breast milk fortified with other nutrients. Accordingly, the human milk fortifier of the present invention can be administered after dissolution in human breast milk, infant formula, growing-up milk or human breast milk fortified with other nutrients, or otherwise it can be administered as a stand-alone composition.

When administered as a stand-alone composition, the human milk fortifier of the present invention can be also identified as being a "supplement". In one embodiment, the milk fortifier of the present invention is a supplement. In some other embodiments, the nutritional composition of the present invention is a fortifier. The fortifier can be a breast milk fortifier (e.g. a human milk fortifier) or a formula fortifier such as an infant formula fortifier or a follow-on/follow-up formula fortifier.

In some other embodiments, the nutritional composition of the present invention is a dietary supplement. When the nutritional composition is a supplement, it can be provided in the form of unit doses. The supplement may be in the form of tablets, capsules, pastilles or a liquid for example. The supplement may further contain protective hydrocolloids (such as gums, proteins, modified starches), binders, film-forming agents, encapsulating agents/materials, wall/shell materials, matrix compounds, coatings, emulsifiers, surface-active agents, solubilizing agents (oils, fats, waxes, lecithins etc.), adsorbents, carriers, fillers, co-compounds, dispersing agents, wetting agents, processing aids (solvents), flowing agents, taste-masking agents, weighting agents, jellifying agents and gel forming agents. The supplement may also contain conventional pharmaceutical additives and adjuvants, excipients, and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients under the recommendations of Government bodies such as the USRDA.

Other product formatss like beverages and powders (sachet format) can also be chosen. In a further embodiment, the nutritional composition is selected from the group consisting of a beverage product, an amino acid-based beverage, a yogurt product, fermented milk, a fruit juice, a dried powder in sachet format or a cereal bar. These nutritional compositions are well suited for administering plant phenols to, for example, older children and adult humans.

A particular need for products to reduce symptoms of eosinophilic esophagitis may be in the clinical environment, such as in hospitals, clinics and homes for elderly persons. Therefore, in a still further embodiment, the nutritional composition is a food for specific medical purposes such as a health care nutritional composition for oral feeding, and/or a nutritional product for enteral or parental feeding. In the latter case, it will only include ingredients that are suitable for parenteral feeding. Ingredients that are suitable for parental feeding are known to the person skilled in the art.

The nutritional composition of the present invention can be in solid (e.g. powder), liquid or gelatinous form.

Human Milk Oligosaccharides

The nutritional composition of the invention contains human milk oligosaccharides (HMOs).

Many different kinds of HMOs are found in human milk. Each oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk. Almost all HMOs have a lactose moiety at their reducing end while sialic acid and/or fucose (when present) occupy terminal positions at the non-reducing ends. HMOs can be acidic (e.g. charged sialic acid-containing oligosaccharides) or neutral (e.g. fucosylated oligosaccharides).

In some embodiments, HMOs in the nutritional composition comprise, consist essentially of, or preferably consist of 2'-fucosyllactose (2FL), 3'-fucosyllactose (3FL), 3'-sialyllactose (3SL) and lacto-N-neotetraose (LNnT). Thus, the nutritional composition may comprise no other type of HMO aside from 2FL, 3FL, 3SL, and LNnT.

In another embodiment, the HMOs in the nutritional composition comprise, consist essentially of, or preferably consist of 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT). Thus, the nutritional composition may comprise no other type of HMO aside from 2FL, 3FL, 3SL, LNnT, 6SL, and LNT.

The HMOs may be obtained by any suitable method. Suitable methods for synthesising HMOs will be well known to those of skill in the art. For example, processes have been developed for producing HMOs by microbial fermentation, enzymatic processes, chemical syntheses, or combinations of these technologies (Zeuner et al., 2019. Molecules, 24(11), p. 2033).

The 2FL may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Alternatively, 2FL may be produced by chemical synthesis from lactose and free fucose.

The 3FL may be synthesized by enzymatic, biotechnological, and/or chemical processes. The 3FL may be manufactured through fermentation using a genetically modified microorganism. Alternatively, the 3FL may be produced as described in WO 2013/139344.

The 3SL may be synthesized by enzymatic, biotechnological, and/or chemical processes. The 3SL may be produced as described in WO 2014/153253.

The LNnT may be synthesised chemically by enzymatic transfer of saccharide units from donor moieties to acceptor moieties using glycosyltransferases as described, for example, in U.S. Pat. No. 5,288,637 and WO 1996/010086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M. and Stutz, A. E. (1999) Angew. Chem. Int. Ed. 38: 827-828. N-acetyl-lactosamine produced in this way may then be transferred to lactose as the acceptor moiety. Alternatively, the LNnT may be produced as described in WO 2011/100980 or WO 2013/044928.

The 6SL may be synthesized by chemical methods including stereoselective 6'-O-sialylation of either 4',6'-sugar diols or 6'-sugar alcohols using glycosylhalide, thioglycoside or diethylphosphite donor activations. Alternatively, the 6SL may be enzymatically produced using glycosyltransferases and sialidases. The 6SL may be produced as described in WO 2011/100979.

The LNT may be synthesized by enzymatic, biotechnological and/or chemical processes. The LNT may be produced as described in WO 2012/155916 or WO 2013/044928. A mixture of LNT and LNnT can be made as described in WO 2013/091660.

In some embodiments the nutritional composition comprises the human milk oligosaccharides (HMOs) 2'-fucosyllactose (2FL), 3'-fucosyllactose (3FL), 3'-sialyllactose (3SL), and lacto-N-neotetraose (LNnT). In some embodiments, the HMOs in the nutritional composition consist of, or consist essentially of, 2FL, 3FL, 3SL, and LNnT.

In some embodiments, the HMOs in the nutritional composition consist of, or consist essentially of:

i. about 40 wt % to about 80 wt % of 2FL, preferably about 55 wt % to about 75 wt %, preferably about 65 wt % to about 70 wt %;
ii. about 2 wt % to about 15 wt % of LNnT, preferably about 4 wt % to about 12 wt %, preferably about 6 wt % to about 9 wt %;
iii. about 5 wt % to about 30 wt % 3FL, preferably about 10 wt % to about 25 wt %, preferably about 15 wt % to about 20 wt %; and
iv. about 2 wt % to about 15 wt % of 3SL; preferably about 4 wt % to about 12 wt %, preferably about 7 wt % to about 9 wt %.

In some embodiments, the total amount of 2FL, 3FL, 3SL, and LNnT present in the nutritional composition is at a concentration of between 1 μg/ml and 5000 μg/ml, preferably between 10 μg/ml and 100 μg/ml. In some embodiments, the total amount of 2FL, 3FL, 3SL, and LNnT present in the nutritional composition is at a concentration of between 1 μg/kcal and 10000 μg/kcal, preferably between 10 μg/kcal and 200 μg/kcal.

In some embodiments the invention provides a nutritional composition comprising the human milk oligosaccharides (HMOs) 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT). In some embodiments, the HMOs in the nutritional composition consist of, or consist essentially of, 2FL, 3FL, 3SL, LNnT, 6SL, and LNT.

In some embodiments, the HMOs in the nutritional composition consist of, or consist essentially of:

i. about 35 wt % to about 60 wt % of 2FL, preferably about 40 wt % to about 50 wt %, preferably about 43 wt % to about 47 wt %;
ii. about 1 wt % to about 10 wt % of LNnT, preferably about 3 wt % to about 7 wt %, preferably about 4 wt % to about 6 wt %;
iii. about 10 wt % to about 30 wt % of LNT, preferably about 15 wt % to about 25 wt %, preferably about 18 wt % to about 22 wt %;
iv. about 3 wt % to about 20 wt % 3FL, preferably about 7 wt % to about 15 wt %, preferably about 10 wt % to about 13 wt %;
v. about 1 wt % to about 10 wt % of 3SL, preferably about 4 wt % to about 8 wt %, preferably about 5 wt % to about 7 wt %; and
vi. about 5 wt % to about 20 wt % of 6SL, preferably about 7 wt % to about 15 wt %, preferably about 10 wt % to about 14 wt %.

In some embodiments, in particular where the nutritional composition is an infant formula or a young-child formula, the total amount of 2FL, 3FL, 3SL, and LNnT present in the nutritional composition is at a concentration of between 10 μg/ml and 10000 μg/ml, preferably between 50 μg/ml and 5000 μg/ml (when formulated as instructed).

In some embodiments, in particular where the nutritional composition is an infant formula or a young-child formula, the total amount of 2FL, 3FL, 3SL, LNnT, 6SL, and LNT present in the nutritional composition is at a concentration of between 10 μg/ml and 10000 μg/ml, preferably between 50 μg/ml and 5000 μg/ml (when formulated as instructed).

In some embodiments, when the nutritional composition is in the form of a supplement, the total amount of 2FL, 3FL, 3SL, and LNnT, or of 2FL, 3FL, 3SL, LNnT, 6SL, and LNT, present in the supplement may be in an amount of 0.2 g to 2 g per unit dose of the supplement, preferably about 0.4 g to 1.5 g per unit dose, preferably between 0.5 g and 1 g per unit dose. In one embodiment, when the nutritional composition is in the form of a supplement, the total amount of 2FL, 3FL, 3SL, and LNnT, or the total amount of 2FL, 3FL, 3SL, LNnT, 6SL, and LNT, present in the supplement may be in an amount of 0.7 g to 0.8 g per unit dose of the supplement.

In a particular embodiment of the present invention, the nutritional composition comprises the 2'-fucosyllactose (2FL) and lacto-N-neotetraose (LNnT) in a 2FL:LNnT weight ratio from 1:10 to 12:1, such as from 1:7 to 10:1 or from 1:5 to 5:1 or from 2:1 to 5:1 or from 1:3 to 3:1, or from 1:2 to 2:1, or from 1:1 to 3:1, or from 1:5 to 1:0.5; for example 2:1 or 10:1. In a particular embodiment of the present invention, the nutritional composition comprises the 2'-fucosyllactose (2FL) and lacto-N-neotetraose (LNnT) in a 2FL:LNnT weight ratio of about 2:1.

Protein

The term "protein" includes peptides and free amino acids. The protein content of the nutritional composition may be calculated by any method known to those of skill in the art. Suitably, the protein content may be determined by a nitrogen-to-protein conversion method. For example, as described in Maubois, J. L. and Lorient, D. (2016) Dairy Science & Technology 96(1): 15-25. Preferably the protein content is calculated as nitrogen content×6.25, as defined in European Commission Regulation (EU) 2016/127 of 25 Sep. 2015. The nitrogen content may be determined by any method known to those of skill in the art. For example, nitrogen content may be measured by the Kjeldahl method.

The protein content of the nutritional composition of the invention, particularly the infant formula of the invention, is preferably in the range 1.6-3.2 g protein per 100 kcal. In some embodiments, the protein content of the nutritional composition is in the range 1.8-2.8 g protein per 100 kcal.

eHFs typically contain 2.6-2.8 g protein per 100 kcal and AAFs typically contain 2.8-3.1 g protein per 100 kcal, for example, to cover the needs of infants suffering gastrointestinal pathologies with severe malabsorption or infants requiring more proteins and calories to cover a higher metabolic rate.

Infant formulas, such as an eHF or an AAF, with a lower protein content may support appropriate growth and development of allergic infants, as well as being safe and well-tolerated.

Accordingly, in some embodiments, the nutritional composition of the invention, particularly the infant formula of the invention, may comprise about 2.4 g or less protein per 100 kcal. For example, the nutritional composition may comprise about 2.3 g or less protein per 100 kcal, 2.25 g or less protein per 100 kcal, or 2.2 g or less protein per 100 kcal.

Suitably, the nutritional composition of the invention, particularly the infant formula of the invention, comprises about 1.8 g or more protein per 100 kcal. For example, the nutritional composition may comprise about 1.86 g or more protein per 100 kcal, 1.9 g or more protein per 100 kcal, 2.0 g or more protein per 100 kcal, or 2.1 g or more protein per 100 kcal. In some embodiments, the nutritional composition comprises about 1.86 g or more protein per 100 kcal, in line with present EU regulations for infant formula (EFSA NDA Panel (2014) EFSA journal 12(7): 3760).

In some embodiments, the nutritional composition of the invention, particularly the infant formula of the invention, may comprise 1.8-2.4 g protein per 100 kcal, 1.86-2.4 g protein per 100 kcal, 1.9-2.4 g protein per 100 kcal, 2.0-2.4 g protein per 100 kcal, 2.0-2.3 g protein per 100 kcal, 2.1-2.3 g protein per 100 kcal, or 2.15-2.25 g protein per 100 kcal.

Protein Source

The source of protein may be any source suitable for use in a nutritional composition.

In some embodiments, the protein is cow's milk protein. In some embodiments, the nutritional composition does not comprise cow's milk protein In some embodiments, the nutritional composition does not comprise dairy protein. Accordingly, in some embodiments, 100% by weight of the total protein is non-dairy protein.

An extensively hydrolysed/hydrolysed whey-based formula may be more palatable than an extensively hydrolysed/hydrolysed casein-based formula and/or the subject may only be sensitised to casein protein. Suitably, therefore, more than about 50%, more than about 60%, more than about 70%, more than about 80%, more than about 90%, or about 100% of the protein is whey protein. Preferably, the protein source is whey protein.

The whey protein may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey that has been demineralised by ion exchange and/or by electrodialysis and is known as demineralised whey protein (DWP).

The source of the whey protein may be sweet whey from which the caseino-glycomacropeptide (CGMP) has been totally or partially removed. This is called modified sweet whey (MSW). Removal of the CGMP from sweet whey results in a protein material with threonine and trytophan contents that are closer to those of human milk. A process for removing CGMP from sweet whey is described in EP880902.

The whey protein may be a mix of DWP and MSW.

In some embodiments, the amount of casein in the nutritional composition is undetectable, for example less than 0.2 mg/kg. The amount of casein may be determined by any method known to those of skill in the art.

Degree of Hydrolysis

Hydrolysed proteins may be characterised as "partially hydrolysed" or "extensively hydrolysed" depending on the degree to which the hydrolysis reaction is carried out. Currently there is no agreed legal/clinical definition of Extensively Hydrolyzed Products according to the WAO (World Allergy Organization) guidelines for Cow's milk protein allergy (CMA) but there is agreement that according to the WAO that hydrolysed formulas have proven to be a useful and widely used protein source for infants suffering from CMA. In the current invention partially hydrolysed proteins are one in which 60-70% of the protein/peptide population has a molecular weight of less than 1000 Daltons, whereas extensively hydrolysed proteins are one in which at least 95% of the protein/peptide population has a molecular weight of less than 1000 Dalton. These definitions are currently used in the industry. Partially hydrolysed proteins are usually considered as hypoallergenic (HA) whereas extensively hydrolysed proteins are usually considered as non-allergenic.

The hydrolysed proteins of the invention may have an extent of hydrolysis that is characterised by NPN/TN %. Non-Protein Nitrogen over Total Nitrogen is widely use as a measure of soluble peptides created by enzymatic hydrolysis. NPN/TN % means the Non Protein Nitrogen divided by the Total Nitrogen×100. NPN/TN % may be measured as detailed in Adler-Nissen J-, 1979, J. Agric. Food Chem., 27 (6), 1256-1262. In general, extensively hydrolysed proteins are characterised as having a NPN/TN % of greater than 95%, whereas partially hydrolysed proteins are characterized as having a NPN/TN % in the range 75%-85%. Partially hydrolysed proteins may also be characterised in that 60-70% of their protein/peptide population has a molecular weight of less than 1000 Daltons.

In a preferred embodiment, the protein may have an NPN/TN % greater than 90%, greater than 95% or greater than 98%. In a preferred embodiment where "extensively" hydrolysed proteins are desired the hydrolysed proteins of the invention has a NPN/TN % in the range of greater than 95%. Suitably, the protein may have an NPN/TN % greater than 90%, greater than 95% or greater than 98%. These extensively hydrolysed proteins may also be characterised in that at least 95% of their protein/peptide population has a molecular weight of less than 1000 Daltons.

The extent of hydrolysis may also be determined by the degree of hydrolysis. The "degree of hydrolysis" (DH) is defined as the proportion of cleaved peptide bonds in a protein hydrolysate and may be determined by any method known to those of skill in the art. Suitably the degree of hydrolysis is determined by pH-stat, trinitrobenzenesulfonic acid (TNBS), o-phthaldialdehyde (OPA), trichloroacetic acid soluble nitrogen (SN-TCA), or formol titration methods. (Rutherfurd, S. M. (2010) Journal of AOAC International 93(5): 1515-1522). The degree of hydrolysis (DH) of the protein can, for example, be more than 90, more than 95 or more than 98.

The extent of hydrolysis may also be determined by the peptide molecular mass distribution. The peptide molecular mass distribution may be determined by high performance size exclusion chromatography, optionally with UV detection (HPSEC/UV) (Johns, P. W. et al. (2011) Food chemistry 125(3): 1041-1050). For example, the peptide molecular mass distribution may be a HPSEC peak area-based estimate determined at 205 nm, 214 nm or 220 nm. Suitably when the peptide molecular mass distribution is determined by HPSEC/UV, the "percentage of peptides by weight" that have a certain molecular mass may be estimated by the "fraction of peak area as a percentage of total peak area", that have the molecular mass, determined at 205 nm, 214 nm or 220 nm. Suitably, the extent of hydrolysis may be determined by the methods described in WO 2016/156077. Alternatively, the peptide molecular mass distribution may be determined by any method known to those of skill in the art, for example by sodium dodecyl sulphate-polyacrylamide gel electrophoresis (SDS-PAGE) (Chauveau, A. et al. (2016) Pediatric Allergy and Immunology 27(5): 541-543).

Theoretically, to bind with cell membrane-bound IgE, peptides should be greater than about 1500 Da in size (approximately 15 amino acids) and to crosslink IgE molecules and to induce an immune response, they must be greater than about 3000 Da in size (approximately 30 amino acids) (Nutten (2018) EMJ Allergy Immunol 3(1): 50-59).

Suitably, therefore, at least about 95%, at least about 98%, at least about 99% or about 100% of the peptides by weight in the eHF have a molecular mass of less than about 3000 Da. There may, for example, be no detectable peptides about 3000 Da or greater in size in the eHF.

Suitably, therefore, at least about 95%, at least about 98%, at least about 99% or about 100% of the peptides by weight in the eHF have a molecular mass of less than about 1500 Da. Preferably, at least 99% of the peptides by weight have a molecular mass of less than about 1500 Da. There may, for example, be no detectable peptides about 1500 Da or greater in size in the eHF.

Preferably, at least about 85%, at least about 90%, at least about 95%, at least about 98%, or at least about 99% of the peptides by weight in the eHF have a molecular mass of less than about 1200 Da. More preferably, at least 95% or 98% of the peptides by weight in the eHF have a molecular mass of less than about 1200 Da.

Suitably, at least about 80%, at least about 85%, at least about 90%, or at least about 95% of the peptides by weight in the eHF have a molecular mass of less than about 1000 Da. Preferably, at least about 95% of the peptides by weight in the eHF have a molecular mass of less than about 1000 Da.

Preferably, the eHF has no detectable peptides about 3000 Da or greater in size; and at least about 95% of the peptides by weight have a molecular mass of less than about 1200 Da.

Having a high proportion of di- and tri-peptides may improve nitrogen (protein) absorption, even in patients with gut impairment. PEPT1 is a dedicated facilitator transport route for small peptide absorption (e.g. di- and tri-peptides). In the first weeks of life, intestinal PEPT1 is important for nutritional intake, and later for diet transition following weaning.

Thus, at least about 30%, at least about 40%, or at least about 50% of the peptides by weight in the eHF may, for example, be di- and tri-peptides. Preferably, at least about 45%, at least about 50%, 45-55%, or 50-54% of the peptides by weight in the eHF are di- and tri-peptides. More preferably, about 51-53%, or most preferably, about 52% of the peptides by weight in the eHF are di- and tri-peptides.

Suitably, at least about 30%, at least about 40%, or at least about 50% of the peptides by weight in the eHF have a molecular mass of between 240 and 600 Da. Preferably, at least about 45%, at least about 50%, 45-55%, or 50-54% of the peptides by weight in the eHF have a molecular mass of between 240 and 600 Da. More preferably, about 51-53%, or most preferably, about 52% of the peptides by weight in the eHF have a molecular mass of between 240 and 600 Da.

The peptides in the eHF may, for example, have a median molecular weight of 300 Da to 370 Da, preferably 320 Da to 360 Da.

The principal recognised cow's milk allergens are alpha-lactalbumin (aLA), beta-lactoglobulin (bLG), and bovine serum albumin (BSA).

Suitably, therefore, the eHF may have non-detectable aLA content, for example about 0.010 mg/kg aLA or less; the eHF may have non-detectable bLG content, for example about 0.010 mg/kg bLG or less; and/or the eHF may have non-detectable BSA content, for example about 0.010 mg/kg BSA or less. Preferably, the eHF comprises no detectable amounts of aLA, bLG, and BSA. The content of aLA, bLG, and BSA may be determined by any method known to those of skill in the art, for example ELISA.

Method of Hydrolysis

Proteins for use in the nutritional composition, preferably the infant formula of the invention, may be hydrolysed by any suitable method known in the art. For example, proteins may be enzymatically hydrolysed, for example using a protease. For example, protein may be hydrolysed using alcalase (e.g. at an enzyme:substrate ratio of about 1-15% by weight and for a duration of about 1-10 hours). The temperature may range from about 40° C. to 60° C., for example about 55° C. The reaction time may be, for example, from 1 to 10 hours, and pH values before starting hydrolysis may, for example, fall within the range 6 to 9, preferably 6.5 to 8.5, more preferably 7.0 to 8.0.

Porcine enzymes, in particular porcine pancreatic enzymes may be used in the hydrolysis process. For example, WO1993004593A1 discloses a hydrolysis process using trypsin and chymotrypsin, which includes a two-step hydrolysis reaction with a heat denaturation step in between to ensure that the final hydrolysate is substantially free of intact allergenic proteins. The trypsin and chymotrypsin used in these methods are preparations produced by the extraction of porcine pancreas.

WO2016156077A1 discloses a process for preparing a milk protein hydrolysate comprising hydrolysing a milk-based proteinaceous material with a microbial alkaline serine protease in combination with bromelain, a protease from *Aspergillus*, and a protease from *Bacillus*.

Free Amino Acids

The nutritional composition of the invention may comprise free amino acids.

The levels of free amino acids may be chosen to provide an amino acid profile that is sufficient for infant nutrition, in particular an amino acid profile that satisfies nutritional regulations (e.g. European Commission Directive 2006/141/EC).

Free amino acids may, for example, be incorporated in the eHF of the invention to supplement the amino acids comprised in the peptides.

Example free amino acids for use in the nutritional composition of the invention include histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof.

Free amino acids provide a protein equivalent source (i.e. contribute to the nitrogen content). As described above, having a high proportion of di- and tri-peptides may improve nitrogen (protein) absorption, even in patients with gut impairment. Accordingly, having a low proportion of free amino acids may also improve nitrogen (protein) absorption, even in patients with gut impairment.

Suitably, therefore, the free amino acids in the eHF may be present in a concentration of 50% or less, 40% or less, 30% or less, or 25% or less by weight based on the total weight of amino acids. Preferably, the eHF comprises 25% or less by weight of free amino acids based on the total weight of amino acids. More preferably, the free amino acids in the eHF are present in a concentration of 20-25%, 21-23%, or about 22% by weight based on the total weight of amino acids.

The free amino acids content may be determined by any method known of skill in the art. Suitably, the free amino acids content may be obtained by separation of the free amino acids present in an aqueous sample extract by ion exchange chromatography and photometric detection after post-column derivatisation with ninhydrin reagent. Total amino acid content may be obtained by hydrolysis of the test portion in 6 mol/L HCl under nitrogen and separation of individual amino acids by ion-exchange chromatography, as described above.

Carbohydrate

The carbohydrate may be any carbohydrate that is suitable for use in a nutritional composition.

The carbohydrate content of the nutritional composition of the invention, particularly the infant formula of the invention, is preferably in the range 9-14 g carbohydrate per 100 kcal.

Example carbohydrates for use in the nutritional composition include lactose, saccharose, maltodextrin and starch. Mixtures of carbohydrates may be used.

In some embodiments, the carbohydrate content comprises maltodextrin. In some embodiments, at least about 20%, at least about 25%, at least about 30%, at least about 35%, at least about 40%, at least about 50%, at least about 60% or at least about 70% by weight of the total carbohydrate content is maltodextrin.

In some embodiments, the carbohydrate content comprises lactose. In some embodiments, at least about 20%, at least about 25%, at least about 30%, at least about 35%, at least about 40%, at least about 50%, at least about 60% or at least about 70% by weight of the total carbohydrate content is lactose.

In some embodiments, the carbohydrate comprises lactose and maltodextrin.

Fat

The fat content of the nutritional composition of the invention, particularly the infant formula of the invention, is preferably in the range 4.0-6.0 g fat per 100 kcal.

Example fats for use in the nutritional composition of the invention include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides (MCT) and esters of fatty acids such as arachidonic acid, linoleic acid, palmitic acid, stearic acid, docosahexaenoic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride. Structured lipids may be added or may be omitted.

Oils containing high quantities of preformed arachidonic acid (ARA) and/or docosahexaenoic acid (DHA), such as fish oils or microbial oils, may be added.

Long chain polyunsaturated fatty acids, such as dihomo-γ-linolenic acid, arachidonic acid (ARA), eicosapentaenoic acid and docosahexaenoic acid (DHA), may also be added.

Oils containing high quantities of SCFA such as acetate, propionate or butyrate or any other lipidic product derived from microbial fermentation.

Medium Chain Triglycerides (MCTs)

A high concentration of MCT may impair early weight gain. MCT is not stored and does not support fat storage. For instance, Borschel et al. have reported that infants fed formula without MCT gained significantly more weight between 1-56 days than infants fed formulas containing 50% of the fat from MCT (Borschel, M. et al. (2018) Nutrients 10(3): 289).

Thus, about 30% or less by weight of the fat may, for example, be medium-chain triglycerides (MCTs) in the nutritional composition of the present invention.

In some embodiments, about 25% or less by weight, 20% or less by weight, 15% or less by weight, 10% or less by weight, 5% or less by weight, 4% or less by weight, 3% or less by weight, 2% or less by weight, 1% or less by weight, 0.5% or less by weight, or 0.1% or less by weight of the fat is medium chain triglycerides (MCTs).

In some embodiments, 0-30% by weight, 0-25% by weight, 0-20% by weight, 0-15% by weight, 0-10% by weight, 0-5% by weight, 0-4% by weight, 0-3% by weight, 0-2% by weight, 0-1% by weight, 0-0.5% by weight, or 0-0.1% by weight of the fat is medium chain triglycerides (MCTs).

In some embodiments, the nutritional composition comprises no added MCTs. Suitably, about 0% by weight of the fat is MCTs and/or the composition comprises no detectable MCTs. Suitably, the nutritional composition comprises no MCTs.

Further Ingredients

The nutritional composition, particularly an infant formula or young-child formula of the invention, may also contain all vitamins and minerals understood to be essential in the daily diet in nutritionally significant amounts. Minimum requirements have been established for certain vitamins and minerals.

Example vitamins, minerals and other nutrients for use in the nutritional composition of the invention, particularly the infant formula of the invention, include vitamin A, vitamin 1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine and L-carnitine. Minerals are usually added in their salt form.

The nutritional composition may comprise one or more carotenoids.

The nutritional composition may also comprise at least one probiotic. The term "probiotic" refers to microbial cell preparations or components of microbial cells with beneficial effects on the health or well-being of the host. In particular, probiotics may improve gut barrier function.

Examples of probiotic micro-organisms for use in the nutritional composition of the invention include yeasts, such as *Saccharomyces, Debaromyces, Candida, Pichia* and *Torulopsis*; and bacteria, such as the genera *Bifidobacterium, Bacteroides, Clostridium, Fusobacterium, Melissococcus, Propionibacterium, Streptococcus*

Preferred probiotics are those which as a whole are safe, are L(+) lactic acid producing cultures and have acceptable shelf-life for products that are required to remain stable and effective for up to 24 months, *Enterococcus, Lactococcus, Staphylococcus, Peptostrepococcus, Bacillus, Pediococcus, Micrococcus, Leuconostoc, Weissella, Aerococcus*, Oenococcus and *Lactobacillus*.

Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus rhamnosus* (*Lactobacillus* GG), *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus* and *Staphylococcus xylosus, Lacticaseibacillus rhamnosus, Lacticaseibacillus paracasei, Limosilactobacillia, Akkermemsia, Clostridales, Prevotella*

The nutritional composition of the invention may also contain other substances which may have a beneficial effect such as prebiotics, lactoferrin, fibres, nucleotides, nucleosides and the like.

Method of Manufacture

The nutritional composition of the invention may be prepared in any suitable manner.

For example, the nutritional composition described herein may be prepared by blending together the protein source, the carbohydrate source and the fat source in appropriate proportions. If used, the further emulsifiers may be included at this point. The vitamins and minerals may be added at this point but vitamins are usually added later to avoid thermal degradation. Any lipophilic vitamins, emulsifiers and the like may be dissolved in the fat source prior to blending. Water, preferably water which has been subjected to reverse osmosis, may then be mixed in to form a liquid mixture. Commercially available liquefiers may be used to form the liquid mixture. The liquid mixture may then be homogenised.

The liquid mixture may then be thermally treated to reduce bacterial loads. This may be carried out, for example, by means of steam injection, or using an autoclave or heat exchanger, for example a plate heat exchanger.

The liquid mixture may then be cooled and/or homogenised. The pH and solid content of the homogenised mixture may be adjusted at this point.

The homogenised mixture may then be transferred to a suitable drying apparatus such as a spray dryer or freeze dryer and converted to powder. If a liquid nutritional composition is preferred, the homogenised mixture may be sterilised, then aseptically filled into a suitable container or maybe first filled into a container and then retorted.

The skilled person will understand that they can combine all features of the invention disclosed herein without departing from the scope of the invention as disclosed.

Granulocytes and Allergic/Immune Response

Each tissue of a healthy individual will have a characteristic number of granulocytes (including eosinophils, mast cells and/or basophils) which can also be zero. This number of granulocytes can be raised due to eosinophilic gastrointestinal disorders (eosinophilic esophagitis, eosinophilic gastritis, eosinophilic gastroenteritis, or eosinophilic colitis), a (food) allergy, or atopic dermatitis.

Thus, an "an above-normal number of granulocyte in a tissue" defines that the number of eosinophils, basophils or mast cells is raised in a subject suffering from one of those disorders compared to a healthy individual. If the tissue of a healthy person contains no granulocytes normally, "an above-normal number of eosinophils in a tissue" is at least 1, 10, 100 eosinophils in an high power field (HPF) or 400× on a microscopic histologic tissue or lavage of a tissue on a slide.

If the tissue of a healthy person contains granulocytes normally, "an above-normal number of granulocytes in a tissue" means an increase of at least 10%, 25%, 50%, 100%, 500%, or 1000% compared to the number of granulocytes found in the same tissue of a healthy individual.

Such above normal numbers of granulocytes can be observed in the mucosa of the esophagus, of the stomach, or the colon, or can be observed in the skin. Thus, above normal numbers of granulocytes can be observed in any tissues that are exposed to foreign antigens, i.e. antigens that are not found in the individual harboring the tissues.

Eosinophilic Gastrointestinal Disorders (EGIDs) are a chronic and complex group of diseases which can affect adults and children. These disorders are characterized by having above normal amounts of eosinophils and mast cells, types of white blood cell, in one or more specific places anywhere in the digestive system. Mast cells are effector cells of allergic inflammation as directly responsible of histamine degranulation in case of allergic reaction. EGID is further subdivided into organ-specific diagnosis. For example, Eosinophilic Gastritis means eosinophils infiltrating the stomach. While visual inflammation is not always present, inflammation may be apparent under the microscope. EGIDS in the sense of the invention can be eosinophilic esophagitis, eosinophilic gastritis, eosinophilic gastroenteritis, or eosinophilic colitis.

Eosinophilic esophagitis is an inflammatory condition of the esophagus. Symptoms include functional abdominal pain, vomiting, difficultly to thrive, swallowing difficulty, food impaction, acid reflux and heartburn. It is characterized by the presence of eosinophilic and mast cells infiltrates in the epithelium of the esophagus. The infiltration of the eosinophils can be associated with a thickening of the basal layer.

The cytokines IL-4, IL-5, and IL-13, secreted by TH2 cells, provide protective immunity in the context of parasite infection, but also initiate, amplify, and prolong allergic responses by enhancing production of IgE and are responsible for recruitment, expansion, and differentiation of eosinophils and mast cells (Robinson et al., 1992, N. Engl. J. Med. 326, 298-304; Romagnani, 1994, Annu. Rev. Immunol. 12, 227-257; Northrop et al., 2006, J. Immunol. 177, 1062-1069). IL-5 is a TH2 homodimeric cytokine involved in the differentiation, maturation, migration, development, survival, trafficking and effector functions of blood and local tissue eosinophils. The IL-5 receptor (IL-5R) consists of an IL-5-specific α subunit that interacts in conformationally dynamic ways with the pc subunit, an aggregate of domains that also have binding sites for IL-3 and GM-CSF. IL-5 is an eosinophil survival cytokine and IL-5 and IL-5R drive allergic and inflammatory immune responses.

Allergic inflammation is a fundamental pathological change of an allergy. There are two phases in the basic process of allergic inflammation: the induction (sensitization) phase and the effector phase. The induction phase involves antigen-presenting cells (APCs), T cells, TH2 cytokines, such as interleukin (IL)-4, IL-5 and IL-13, class switching of B cells, IgE secretion and binding to the high-affinity IgE receptor FcεRI on the membrane of mast cells and basophils, forming sensitized mast cells and basophils. When the sensitized individual is re-exposed to the same allergen that initiated the response, the IgE is able to bind to that allergen. The effector phase occurs when the same allergen cross-links two adjacent IgEs on sensitized mast cells or basophils; The activated mast cells or basophils subsequently undergo degranulation, releasing proinflammatory mediators or cytokines, thereby causing the clinical manifestations of allergy. Soluble allergens, IgEs and mast cells or basophils are key factors in the pathophysiological process of allergic inflammation, representing causative factors, messengers and primary effector cells, respectively. In contrast to basophils and mast cells, eosinophils and neutrophils are secondary effector cells, which can be accumulated and activated through the mediators released from mast cells or basophils. In a similar mechanism, degranulation of activated eosinophils releases preformed mediators such as major basic protein, and enzymes such as peroxidase implicated in allergic and inflammatory immune responses, e.g. in EGIDs.

EMBODIMENTS

The present inventors have surprisingly found that specific combinations of HMOs are most efficacious in inhibiting interleukin-5 (IL-5) and stabilizing granulocytes. The combinations and have utility in treating or preventing disorders associated with an above-normal number of granulocytes in a tissue and/or degranulation of granulocytes. For example, the combinations have utility in preventing or treating eosinophilic gastrointestinal diseases and other IgE and non-IgE associated allergic disorders.

As discussed above, IL-5 is an eosinophil survival cytokine. Decreasing IL-5 with HMOs allows reducing eosinophilia. The nutritional composition of the invention may be used to treat, prevent or reduce the risk of diseases associated with above-normal numbers of eosinophils in tissue for example eosinophilic gastrointestinal diseases and eosinophil associated allergic disorders.

Further, stabilization of granulocytes, has an important role in the mediation of allergic response, in particular allergic inflammation associated with EGIDs and other allergic disorders.

The nutritional composition comprising the combination of HMOs defined herein, according to the invention, may be used in treating or preventing a disorder associated with an above-normal number of granulocytes in a tissue and/or degranulation of granulocytes.

The nutritional composition of the invention may be used in preventing or treating eosinophilic gastrointestinal disorders, allergies, in particular, food allergies, a gastrointestinal syndrome, allergy associated with aeroallergen including asthma and allergic rhinitis, lung allergic inflammation or skin atopic dermatitis. Preferably the nutritional composition of the invention may be used in preventing or treating eosinophilic gastrointestinal disorders.

In one embodiment, the eosinophilic gastrointestinal disorder is selected from the group consisting of eosinophilic esophagitis, eosinophilic gastritis, eosinophilic gastroenteritis, or eosinophilic colitis.

In a specific embodiment, the eosinophilic gastrointestinal disorder is eosinophilic esophagitis.

In another aspect, the invention provides a method of decreasing the expression of interleukin IL-5 in a subject comprising administering a nutritional composition as defined herein to the subject.

Preferred features and embodiments of the invention will now be described by way of non-limiting examples.

EXAMPLES

Example 1

Peripheral blood mononuclear cells (PBMCs) were isolated and cultured according to a previously published study (Holvoet et al 2013—Int Arch Allergy Immunol 2013; 161:142-154). Buffy coat from blood donations of healthy volunteers were collected at the Transfusion Center of Lausanne (Transfusion interegionnale CRS). Human PBMCs were isolated from buffy coat. Cells were resuspended with equivolume of PBS. PBMCs were isolated by density gradient centrifugation on Histopaque (Sigma). Cells at the interphase were collected and washed two times with PBS+2% FCS. PBMCs were re-suspended in complete RPMI 1640 Medium, GlutaMAX™ Supplement (Thermo Fisher Scientific) containing 10% fetal bovine serum (FBS; Thermo Fisher Scientific), 1% penicillin/streptomycin (Sigma). Cells were cultured in 48-well plates (Milian, Meyrin, Switzerland) at $1.5\times10^6$ cells/ml in the presence of 50 ng/ml of IL-4 (Bioconcept) and 1 μg/ml of anti-CD40 antibody (R&D Systems, Abingdon, UK) in cIMDM to induce a TH2 cytokine phenotype. LPS was used at 100 μg/ml. After 3 days of culture, individual and mix of HMOs were added at a final concentration of 100 μg/ml. After adding ingredients, PBMC culture was continued for an additional 48 h resulting in total culture duration of 5 days.

IL-5 expression levels are shown in FIG. 1. The combinations of 2FL, 3FL, 3SL, and LNnT; and 2FL, 3FL, 3SL, LNnT, 6SL, and LNT gave the lowest IL-5 expression.

Example 2

Stabilization of granulocytes by mixtures of HMOs according to the invention was assessed in rat basophils leukemia cell line RBL-2H3. In this assay, 100 μl of RBL-2H3 cells (ATCC, Manassas, Virginia, United States) were plated at $4\cdot10^4$ cells/well. After 2 hours, cells were passively sensitized with a rat hyperimmune serum (containing anti-BLG IgE) at one-half dilution in HBSS and with radioactive 5-Hydroxytryptamine [3H] trifluoroacetate (Anawa, Kloten, Switzerland) 80 ci/mmol. 1 mci/37mBq/ml. Cells were then preincubated with different dose of HMOs or regular prebiotic fibers and stimulated by different doses of BLG. Stabilization by the fibers and oligosaccharides is calculated at 100% of the maximum release and reported as a log difference vs control (non stabilized). This assay was modified from Fritsché et al. (Fritsché R, Pahud J J, Pecquet S, Pfeifer A. Induction of systemic immunologic tolerance to β-lactoglobulin by oral administration of a whey protein hydrolysate. Journal of Allergy and Clinical Immunology. 1997; 100(2):266-273.)

Figure 2A:
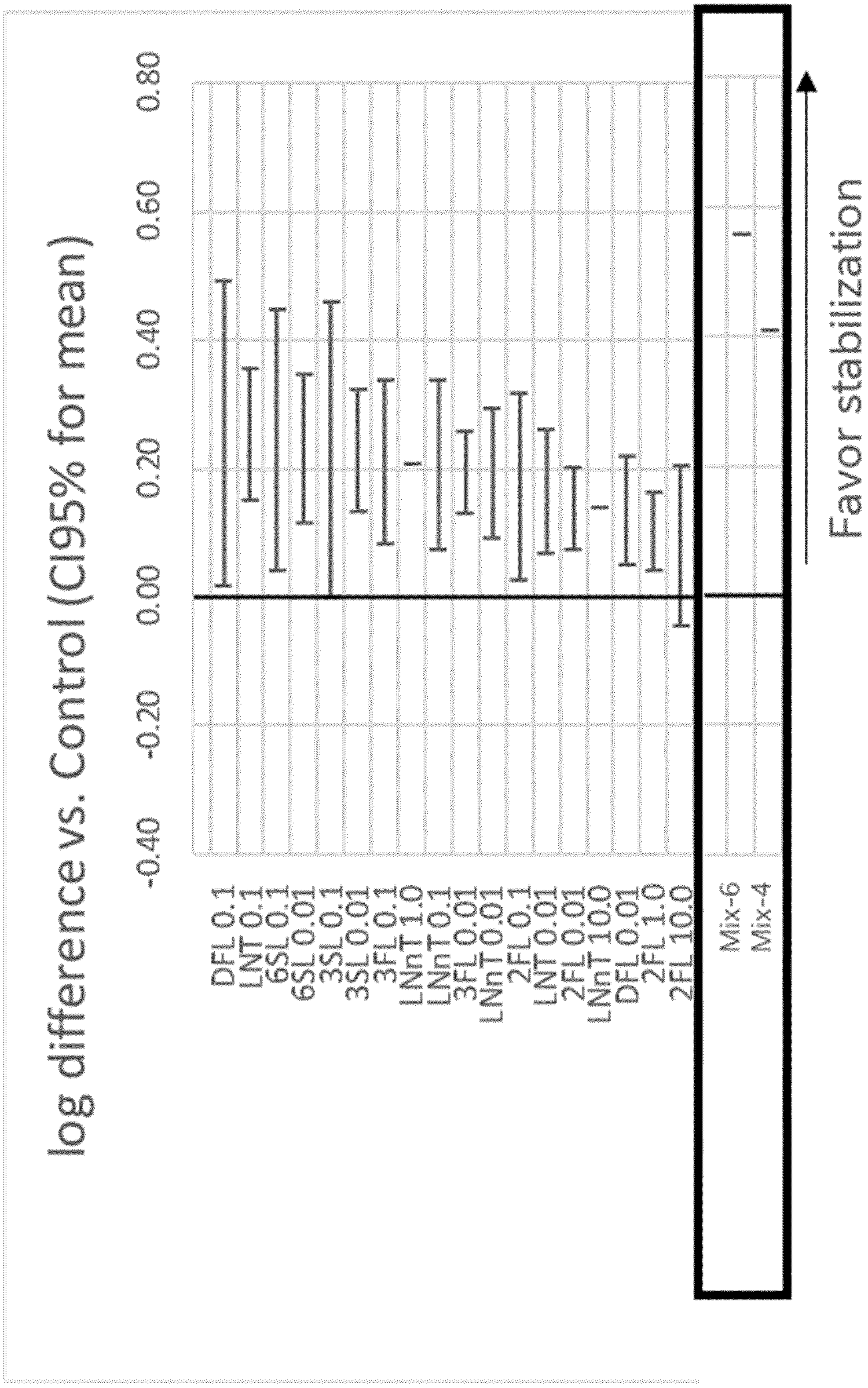
FIG. 2—Stabilization of granulocytes by mixtures of HMOs according to the invention. Rat basophils cell line RBL2H3 were loaded with Radioactive serotonin and passively sensitized with anti-BLG IgE. Cells were then stimulated with BLG. The degranulation in presence of HMO mixes is measured and compared to regular prebiotics fibers (B. Milk, BMOS, Lactose, GOS, Inulin, FOS) and single HMOs (DFL, LNT, 6SL, 3SL, 3FL, LNnT, 2FL).
Figure 2B:
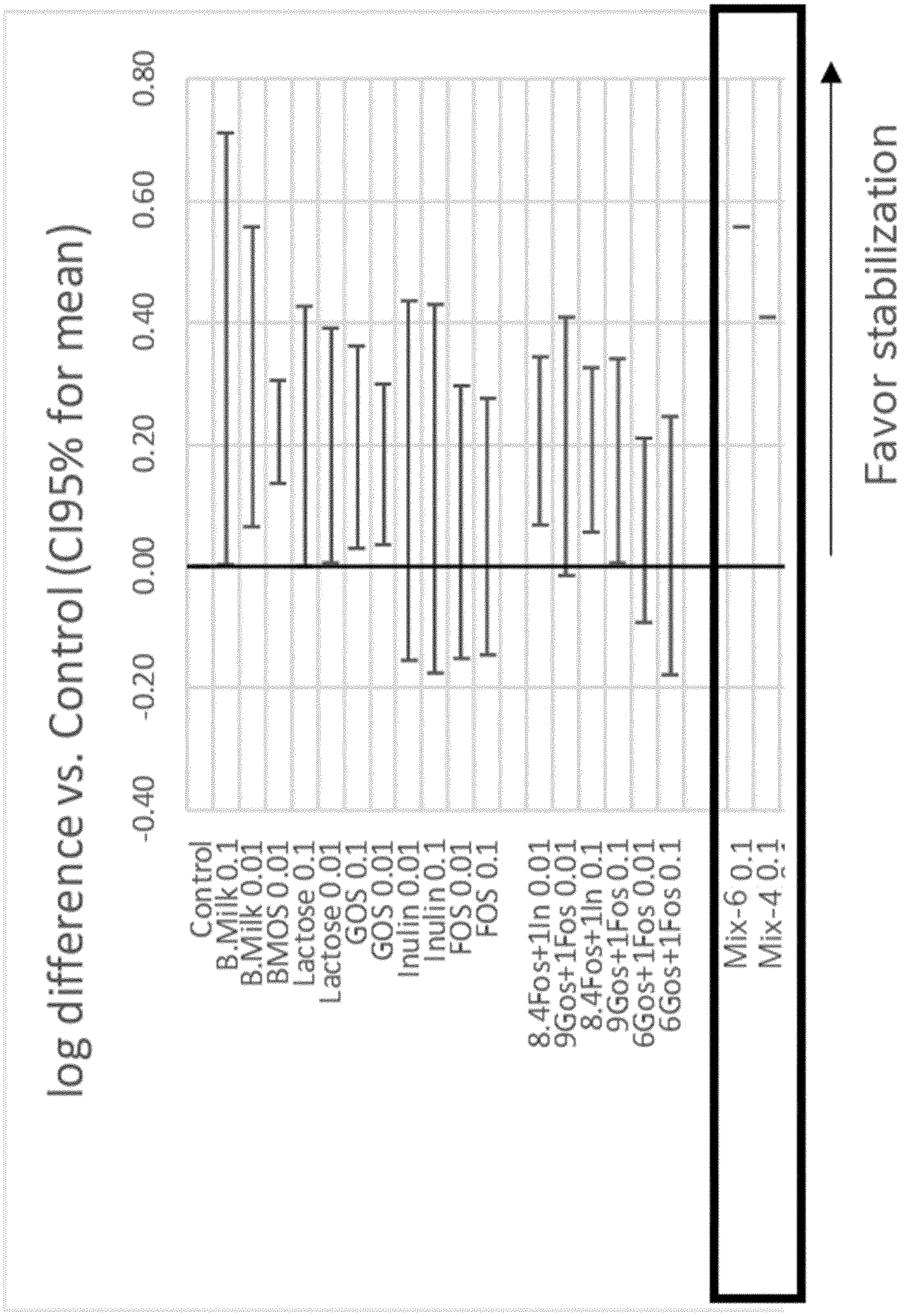

In FIG. 2, the stabilization of the granulocyte is shown. The combinations of 2FL, 3FL, 3SL and LNnT; and 2FL, 3FL, 3SL, LNnT, 6SL and LNT favour the stabilization of granulocytes more than the individual HMO tested at the same concentration (FIG. 2A), and more than the prebiotic fibres and fibre mixes (FOS/GOS/Inulin) (FIG. 2B).

The invention claimed is:

1. A method for treating a disorder associated with an above-normal number of granulocytes in a tissue and/or degranulation of granulocytes, and/or treating an interleukin IL-5 mediated disease, in an individual in need thereof, the method comprising administering a nutritional composition to the individual in need thereof, the nutritional composition comprising the human milk oligosaccharides (HMOs) 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT), wherein the HMOs in the nutritional composition comprise about 2 wt % to about 15 wt % of 3SL.

2. The method according to claim 1, wherein the HMOs in the nutritional composition consist of 2FL, 3FL, 3SL, LNnT, 6SL and LNT.

3. The method according to claim 1, wherein the HMOs in the nutritional composition comprises:

i. about 40 wt % to about 80 wt % of 2FL;
ii. about 2 wt % to about 15 wt % of LNnT; and
iii. about 5 wt % to about 30 wt % 3FL.

4. The method according to claim 1, wherein the HMOs in the nutritional composition comprises:

i. about 35 wt % to about 60 wt % of 2FL;
ii. about 4 wt % to about 8 wt % of LNnT;
iii. about 10 wt % to about 30 wt % of LNT,
iv. about 3 wt % to about 20 wt % 3FL;
v. about 1 wt % to about 10 wt % of 3SL; and
vi. about 5 wt % to about 20 wt % of 6SL.

5. The method according to claim 1, wherein the nutritional composition is in a form selected from the group consisting of:

a. an infant formula, a starter infant formula, a follow-on or follow-up infant formula, a growing-up milk, a fortifier and a supplement,
b. a beverage product, a yoghurt product, a pudding product, fermented milk, a fruit juice, bar, mousse, snack, chips, meal, and meal replacement, and
c. a health care nutritional composition for oral feeding, a nutritional product for enteral feeding and a parenteral feeding product.

6. The method according to claim 1, wherein the total amount of 2FL, 3FL, 3SL, and LNnT present in the nutritional composition is at a concentration of between 10 μg/ml and 10000 μg/ml.

7. The method according to claim 1, wherein the nutritional composition is an extensively hydrolysed formula (eHF) or an amino acid-based formula (AAF).

8. The method according to claim 1, wherein the nutritional composition is an infant or young-child formula and comprises:

(a) 1.6-3.2 g protein per 100 kcal;
(b) 9-14 g carbohydrate per 100 kcal; and
(c) 4.0-6.0 g fat per 100 kcal.

9. The method according to claim 1, wherein the disorder is an eosinophilic gastrointestinal disorder.

10. The method according to claim 9, wherein the eosinophilic gastrointestinal disorder is caused by a food allergy or aeroallergens.

11. The method according to claim 9, wherein the eosinophilic gastrointestinal disorder is selected from the group consisting of eosinophilic esophagitis, eosinophilic gastritis, eosinophilic gastroenteritis, and eosinophilic colitis.

* * * * *